US007169119B2

(12) United States Patent
Chan et al.

(10) Patent No.: US 7,169,119 B2
(45) Date of Patent: Jan. 30, 2007

(54) ARTHRITIC HAND OR FOOT TREATMENT APPARATUS

(76) Inventors: Yung C. Chan, 2938 Old Baltimore Rd., Draper, VA (US) 24324; Mei H. Chan, 2938 Old Baltimore Rd., Draper, VA (US) 24324; King H. Chan, 2938 Old Baltimore Rd., Draper, VA (US) 24324; Ming H. Chan, 2938 Old Baltimore Rd., Draper, VA (US) 24324

( * ) Notice: Subject to any disclaimer, the term of this patent is extended or adjusted under 35 U.S.C. 154(b) by 0 days.

(21) Appl. No.: 11/113,232

(22) Filed: Apr. 25, 2005

(65) Prior Publication Data

US 2006/0241535 A1 Oct. 26, 2006

(51) Int. Cl.
*A61F 1/00* (2006.01)

(52) U.S. Cl. .......................................... 601/15; 601/16

(58) Field of Classification Search ............ 601/15–16; 128/849, 856; 602/3, 13
See application file for complete search history.

(56) References Cited

U.S. PATENT DOCUMENTS 3,865,116 A * 2/1975 Brooks ........................ 607/104
5,074,322 A * 12/1991 Jaw ........................... 134/56 R
5,974,685 A * 11/1999 Hironaka ..................... 34/202

FOREIGN PATENT DOCUMENTS

GB 2177330 A * 1/1987

* cited by examiner

*Primary Examiner*—Michael A. Brown
(74) *Attorney, Agent, or Firm*—William L. Klima; Klima Law Offices, PLLC

(57) ABSTRACT

An arthritic hand or foot treatment apparatus and system for applying dried, pressurized and/or heated air to a user's hand or foot.

14 Claims, 2 Drawing Sheets

ARTHRITIC HAND OR FOOT TREATMENT APPARATUS

FIELD OF THE INVENTION

The present invention is directed to an arthritic hand or foot treatment apparatus. Preferably the treatment apparatus includes an air dryer, air pressurizer and/or air heater.

BACKGROUND OF THE INVENTION

Currently, people having arthritis in the hand or foot suffer significant pain and discomfort from this particular ailment. It is noteworthy that persons having hand or foot arthritis experience relief when visiting or living in warmer and dryer climates.

There exists no readily available inexpensive devices or apparatus for treating the hand or foot of an arthritic person in his or her home. The present invention provides a novel apparatus that is inexpensive, in particular for home or office use to provide some degree of immediate relief from pain and discomfort due to arthritis of the hand or foot.

SUMMARY OF THE INVENTION

A first object of the present invention is to provide an arthritic hand or foot treatment apparatus.

A second object of the present invention is to provide an arthritic hand or foot treatment device for applying dried air to a hand or foot.

A third object of the present invention is to provide an arthritic hand or foot treatment device for applying air pressure to a hand or foot.

A fourth object of the present invention is to provide an arthritic hand or foot treatment device for applying heated air to a hand or foot.

A fifth object of the present invention is to provide an arthritic hand or foot treatment device for applying dried, pressurized and/or heated air to a hand or foot.

A sixth object of the present invention is to provide an arthritic hand or foot treatment apparatus, including a bottle-shaped hand or foot treatment chamber, the treatment chamber having a threaded end and an open end, the treatment chamber including a one-way pressure release valve and a thermostat control; a flexible bag connected to the open end of the treatment chamber, the flexible bag including a open end configured to fit over a arm or leg of a user; an air treatment device, including a bottle-shaped air treatment chamber having an upper threaded end and a lower open end; an electric powered fan disposed within the chamber at least one heating coil disposed adjacent the fan; a one-way valve disposed within the chamber; a layer of air drying composition disposed within the chamber; and a base stand supporting the chamber; a first securing device for attaching and sealing the bag to the open end of the treatment chamber; a second securing device for attaching and sealing the open end of the bag around the user's arm or leg; and a flexible hose connecting the threaded end of the air treatment device to the threaded end of the hand or foot treatment chamber.

A seventh object of the present invention is to provide an arthritic hand or foot treatment apparatus, including a hand or foot treatment chamber; a flexible bag connected to the hand or foot treatment chamber, the bag including an open end configured to fit over an arm or leg of a user; an air treatment device including a fan, air dryer and air heater; and a flexible hose connecting the air treatment device to the hand or foot treatment chamber.

A eighth object of the present invention is to provide an apparatus wherein the hand or foot treatment chamber is provided with a thermostat control for controlling the air treatment device.

A ninth object of the present invention is to provide an apparatus wherein the hand or foot treatment chamber is provided with a one-way pressure relief valve.

A tenth object of the present invention is to provide an apparatus wherein the hand or foot treatment chamber is provided with a one-way pressure relief valve.

A eleventh object of the present invention is to provide an apparatus wherein the hand or foot treatment chamber is provided with a circumferential groove adjacent the open end of the treatment chamber, and including a fastening ring securing the first end of the bag within the groove.

A twelfth object of the present invention is to provide an apparatus wherein the open end of the flexible bag is releasable secured to the arm or leg by at least one hook and loop type fastener.

A thirteenth object of the present invention is to provide an apparatus wherein the hand or foot treatment chamber is a bottle-shaped chamber having a larger lower open end and a smaller threaded upper end.

A fourteenth object of the present invention is to provide an apparatus wherein the air treatment device includes a bottle-shaped chamber having an upper threaded end and a lower open end, the air treatment chamber containing the fan, air dryer and air heater.

A fifteenth object of the present invention is to provide an apparatus wherein the fan is an electric powered fan disposed within the air treatment chamber, the air dryer being at least one heating coil disposed adjacent said fan, and the air dryer being a layer of air drying composition disposed within the chamber.

A sixteenth object of the present invention is to provide an apparatus wherein the air treatment chamber is supported on a base stand.

A seventeenth object of the present invention is to provide an apparatus wherein the air treatment chamber includes a one-way valve.

A eighteenth object of the present invention is to provide an apparatus wherein the air treatment chamber includes a one-way valve.

A nineteenth object of the present invention is to provide an apparatus wherein the apparatus is portable.

A twentieth object of the present invention is to provide an arthritic hand or foot treatment system, including a hand or foot treatment device for at least partially surrounding a hand or foot; and an air treatment device connected to the hand or foot treatment device, the air treatment device providing heated air to the hand or foot treatment device.

A twenty first object of the present invention is to provide an arthritic hand or foot treatment system wherein the air treatment device provides pressurized air to the hand or foot treatment device.

A twenty second object of the present invention is to provide an arthritic hand or foot treatment system wherein the air treatment device provides dried air to the hand or foot treatment device.

A twenty third object of the present invention is to provide an arthritic hand or foot treatment system wherein the air treatment device provides dried air to the hand or foot treatment device.

A twenty fourth object of the present invention is to provide an arthritic hand or foot treatment system wherein the air treatment device is connected to the hand or foot treatment device by a flexible hose.

A twenty fifth object of the present invention is to provide an arthritic hand or foot treatment system wherein the system is portable.

The present invention is directed to a hand or foot treatment apparatus, and system.

The arthritic hand or foot treatment apparatus according to the present invention includes an air treatment device connected to a hand or foot treatment device. Preferably, the air treatment device is connected to the hand or foot treatment device by a hose, preferably, a flexible hose. For example, the flexible hose can be made of plastic or rubber and reinforced with a spiral spring or rings. The arthritic hand or foot system according to the present invention includes an air treatment device for providing dried, pressurized and/or heated air to a user's hand or foot.

The air treatment device according to the present invention is configured for drying air, pressurizing air and/or heating air to be sent to the hand or foot treatment device. In a preferred embodiment, the air treatment device includes a bottle-shaped chamber having a threaded upper end and an open lower end. The air treatment device is provided with an air drying device, an air pressurizing device and an air heating device. For example, the air treatment device contains an electric powered fan for circulating air, at least one heating coil for heating the air, and at least one layer of drying composition for drying the air. In a preferred embodiment, a layer of drying composition is located at the bottom of the air treatment chamber, an electric fan is disposed above the layer of drying composition, at least one heating coil is provided above the electric powered fan, and a one-way air valve is provided above the heating coil. Preferably, the air treatment chamber is provided with a thermostat for controlling the temperature of the air being heating and transferred to the hand or foot treatment device by the flexible hose.

The bottle-shaped air treatment device is provided with a base stand for supporting the air treatment chamber in an upright position or a surface such as the floor, desk top or counter top. Further, the base stand allows air to enter into the open end of the bottle-shaped air treatment chamber through a plurality of vent holes.

The hand or foot treatment device according to the present invention includes a hand or foot treatment chamber combined with a flexible bag connecting an open end of the hand or foot treatment chamber to the arm of leg of the person receiving treatment. In a preferred embodiment, the hand or foot treatment chamber is a bottle-shaped chamber having a threaded end and an opposite open end. In a preferred embodiment, the bottle-shaped hand or foot treatment chamber is provided with a thermostat and control for controlling the air temperature of air being heated by the air treatment device, and a one-way pressure release valve. The bottle-shaped hand or foot treatment chamber is provided with a groove to allow the flexible bag to be secured by a strap or band around the circumference of the bottle-shaped hand or foot treatment chamber. Alternatively, a metal ring having a screw fastener can be used to secure the flexible bag to the outer periphery of the hand or foot treatment chamber adjacent to the open end thereof and in the peripheral groove thereof.

The flexible bag is provided with a pair of opposite open ends. For example, a plastic plenum can be cut to length at two spaced apart ends to provide the flexible bag having the two opposite open ends. Again, the one open end of the flexible bag is connected to the hand or foot treatment chamber, and the opposite open end of the flexible bag is sealed around the arm or leg of the person being treated by a strap, elastic band, or ring (e.g. at least one Velcro strap).

DETAILED DESCRIPTION OF PREFERRED EMBODIMENTS

Figure 1:
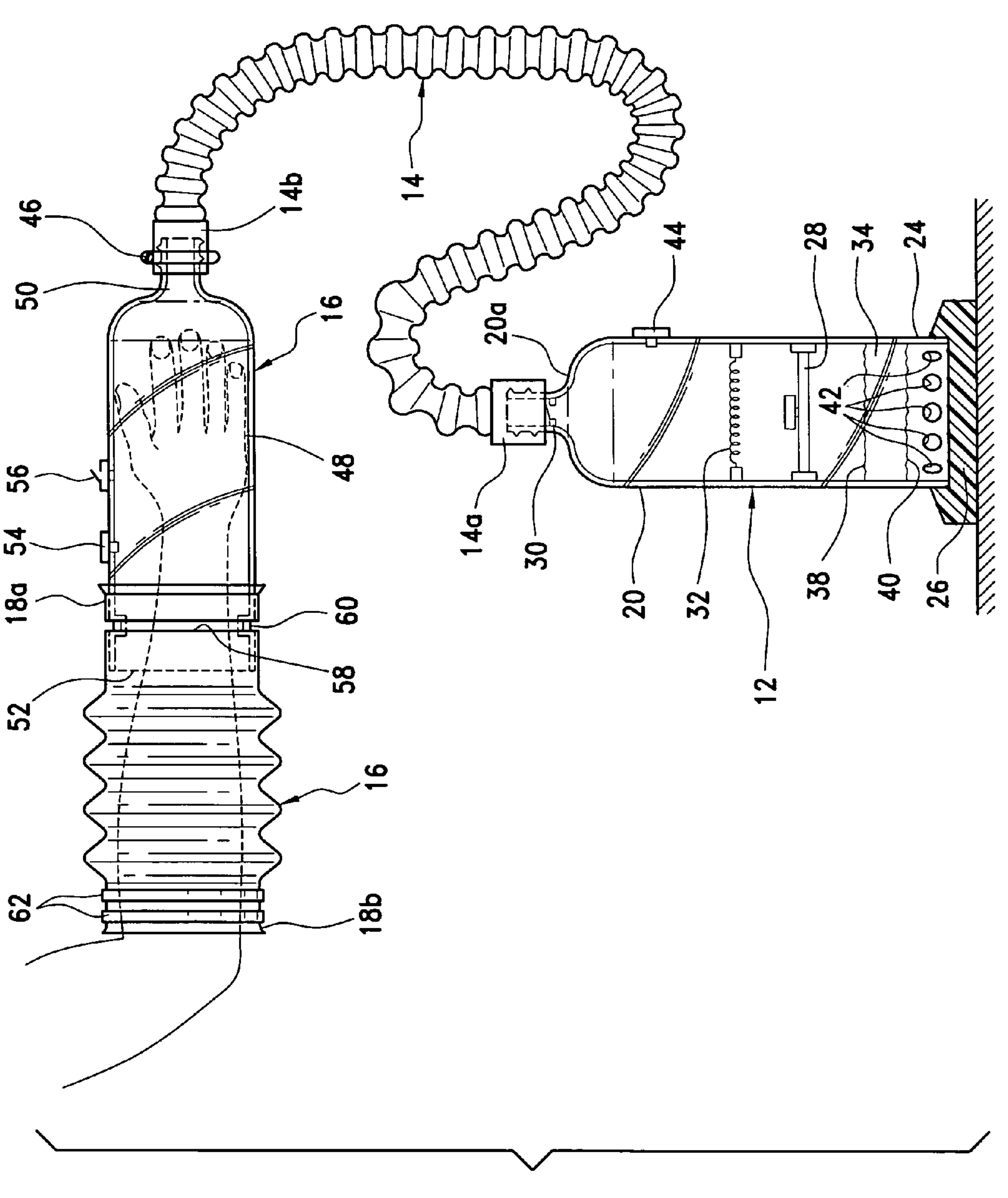
FIG. 1 is a perspective view of a preferred embodiment of the arthritic hand or foot treatment system according to the present invention.
Figure 2:
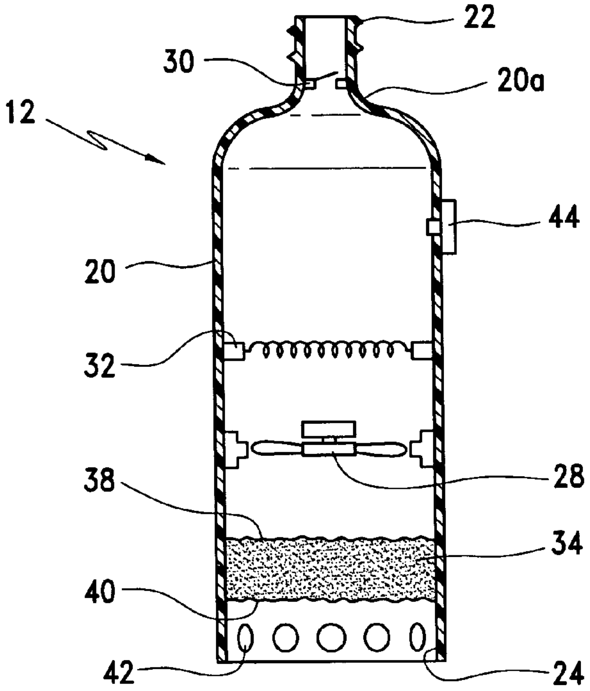
FIG. 2 is a vertical center cross-sectional view of the air treatment device according to the present invention.
Figure 3:
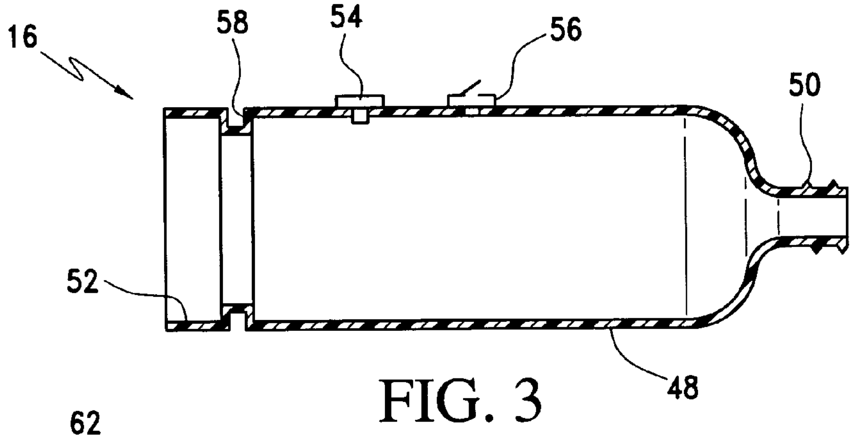
FIG. 3 is a horizontal center cross-sectional view of the hand or foot treatment device according to the present invention.
Figure 4:
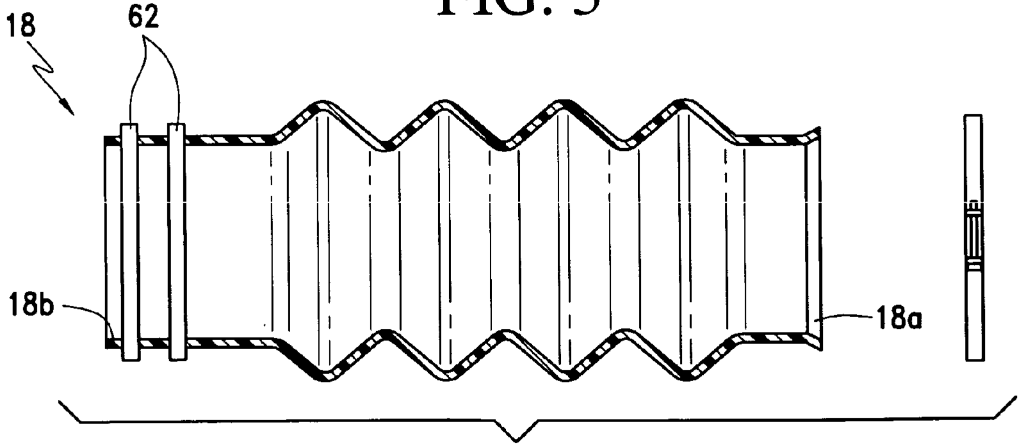
FIG. 4 is a horizontal cross-sectional view of the hand or foot treatment device shown in FIG. 3.

An arthritic hand or foot treatment system 10 according to the present invention is shown in FIG. 1.

The arthritic hand or foot treatment device 10 includes an air treatment device 12, a flexible hose 14, a hand or foot treatment device 16, and a flexible bag 18.

The air treatment device 12 includes a bottle-shaped air treatment chamber 20 having an upper threaded end 22 and a lower open end 24. The air treatment chamber 20 is supported by a base stand 26. For example, the air treatment chamber 20 can be made of a plastic by a blow molding process the same or similar to a two-liter beverage bottle or container. The plastic material can be polyethylene teraphalate (PET), polyethylene, polypropylene, polyvinyl or some other suitable resin or synthetic resin material.

The air treatment chamber 20 is provided with an electric powered blower fan unit 28 supported by the inside wall of the air treatment chamber 20. The fan unit 28 draws in air from the lower open end 24 of the air treatment chamber 20, and pressurizes the air above the fan 28. A one-way valve 30 is provided in the neck portion 20*a* of the air treatment chamber 20. At least one electric powered heating coil 32 is provided above the fan unit 28, and supported by the inner wall of the air treatment chamber 20. A drying layer 34 is provided at the bottom of the air treatment chamber just above the lower open end 24 of the air treatment chamber 20. For example, the drying layer 34 can comprise a layer of anhydrous crystals contained by an upper and lower screen 36, 38.

The lower open end 24 of the air treatment chamber 20 is also provided with air vents 42 through the wall thickness of the air treatment chamber 20 to ensure that an adequate amount of air enters the lower open end 24 of the air treatment chamber 20. In addition, the air treatment chamber 20 is provided with a thermostat 44 for controlling the temperature of the air above the heating coil 32.

The flexible hose 14 is provided with threaded ends 14*a* and 14*b* to connect with the air treatment device 12 and hand or foot treatment device 16, respectively. The flexible hose 14 can be made of plastic or rubber, and preferably is reinforced with a plastic cord or metal spring or rings embedded within the walls of the flexible hose 14. In addition, one or more securing devices such as a rubber ring, elastic band, wire, metal band can be used to further secure the threaded ends 14*a*, 14*b* to the air treatment device 12 and hand or foot treatment device 16, respectively.

The hand or foot treatment device 16 is provided with a bottle-shaped hand or foot treatment chamber 48 having a threaded end 50 and open end 52. The hand or foot treatment chamber 48 is provided with a thermostat 54 to control the temperature of the air within the hand or foot treatment chamber 48, and a one-way pressure relief valve 56. The hand or foot treatment chamber 48 is provided with a peripheral groove 58 to connect with the flexible bag 18 to be described in detail below.

The hand or foot treatment chamber 48 is preferably made of clear see through plastic material. For example, the hand or foot treatment chamber 48 is a plastic blow-molded bottle, the same or similar to a 2 liter beverage bottle or container, with the bottom cut open. The plastic material can be PET, polyvinyl chloride, polyethylene, polypropylene, or some other suitable resin or synthetic resin material.

The flexible bag 18 is provided with a pair of opposite open ends 18*a*, 18*b*. For example, the flexible bag 18 can be made of a clear see through plastic material the same or similar to that used for making plastic garbage bags. Further, the flexible bag can be from a continuous plastic plenum, and then cut to length.

The open end 18*a* is connected to the hand or foot treatment device 16. Specifically, the open end 18*a* is fitted around the periphery of the hand or foot treatment chamber 48 over the peripheral groove 58 and then a securing device 60 (e.g. metal ring with screw tighten, elastic band, elastic ring, hose clamp, wire) secures the open end 18*a* of the flexible bag 18 into the peripheral groove 58 of the hand or foot treatment chamber 48 of the hand or foot treatment device 16. The opposite open end 118*b* fits over the arm or leg of the person being treated, and then one or more securing devices 62 (e.g. hook and loop type fastener, Velcro strap, elastic band, elastic ring) is used to tightly secure the open end 18*b* to the outer surface of the arm or leg.

The arthritic hand or foot treatment device 10 can come as separate units (e.g. air treatment device 12, flexible hose 14, hand or foot treatment device 16, and flexible bag 18), for example, in a single container, and then assembled together when using. Alternatively, the arthritic hand or foot treatment device 10 is fully assembled and stored in container during non-use and then removed from the container for use. The arthritic hand or foot treatment device 10 is preferably portable, highly portable, lightweight and inexpensive to promote home or office (work) use. In a preferred embodiment, the parts or components of the arthritic hand or foot treatment device 10 are made of inexpensive materials and are inexpensive to manufacture and make.

OPERATION

The arthritic hand or foot treatment device 10 is assembled by connecting the flexible hose 14 to the air treatment device 12 and the hand or foot treatment device 16. The flexible bag 18 is connected to the hand or foot treatment device 16.

During use, the flexible bag 18 is connected around the arm of leg of the person receiving treatment using one or more securing devices 62. The electric fan 28 is turned on (e.g. using a switch or plugging the unit into a conventional wall socket). Further, the at least one heating coil 32 is energized to heat the air downstream of the fan unit 28. The thermostat 44 senses the temperature of the air above the at least one heating coil 32, and turns the heating coil 32 on and off to maintain a preset air temperature above the heating coil 32.

The air entering into the air treatment chamber 20 is dried (i.e. moisture is removed from the air stream) by the drying layer 34. Due to the buildup of pressure above the fan unit 28 during operation thereof, the one-way valve 30 opens to release pressurized, heated and dried air into the flexible tube 14, and then into the hand or foot treatment device 16. The hand or foot treatment chamber 48 forms a single treatment chamber with the flexible bag 18. When air pressures build up within the hand or foot treatment chamber 48, the one-way pressure relief valve 56 opens to maintain the pressure within the hand or foot treatment chamber 48 at a predetermined level. Further, the thermostat 54 senses the temperature within the hand or foot treatment chamber 48, and controls the fan unit 28, heating coil 32 and/or valve 30 to maintain the temperature within the hand or foot treatment 48 at a preset level. In this manner, the hand or foot of the user is subjected to pressurized air, heated air and dried air for a period of time significantly aleeving the ailments and pain associated with an arthritic condition. For example, the person's hand or foot is treated for ten to twenty minutes using the hand or foot treatment system 10 according to the present invention.

We claim:

1. An arthritic hand or foot treatment apparatus, comprising:

a bottle-shaped hand or foot treatment chamber, said treatment chamber having a threaded end and an open end, said treatment chamber including a one-way pressure release valve and a thermostat control;

a flexible bag connected to said open end of said treatment chamber, said flexible bag including a open end configured to fit over an arm or leg of a user;

an air treatment device, including:

a bottle-shaped air treatment chamber having an upper threaded end and a lower open end;

an electric powered fan disposed within said chamber;

at least one heating coil disposed adjacent said fan;

a one-way valve disposed within said chamber;

a layer of air drying composition disposed within said chamber; and a base stand supporting said chamber;

a first securing device for attaching and sealing said bag to said open end of said treatment chamber;

a second securing device for attaching and sealing said open end of said bag around the user's forearm or calf; and a flexible hose connecting said threaded end of said air treatment device to said threaded end of said hand or foot treatment chamber.

2. An apparatus according to claim 1, wherein said apparatus is portable.

3. An arthritic hand or foot treatment apparatus, comprising:

a hand or foot treatment chamber;

a flexible bag connected to said hand or foot treatment chamber, said bag including an open end configured to fit over a forearm or calf of a user;

an air treatment device including a fan, air dryer and air heater; and a flexible hose connecting said air treatment device to said hand or foot treatment chamber.

4. An apparatus according to claim 3, wherein said hand or foot treatment chamber is provided with a thermostat control for controlling said air treatment device.

5. An apparatus according to claim 4, wherein said hand or foot treatment chamber is provided with a one-way pressure relief valve.

6. An apparatus according to claim 3, wherein said hand or foot treatment chamber is provided with a one-way pressure relief valve.

7. An apparatus according to claim 3, wherein said hand or foot treatment chamber is provided with a circumferential groove adjacent said open end of said treatment chamber, and including a fastening ring securing said first end of said bag within said groove.

8. An apparatus according to claim 3, wherein said open end of said flexible bag is releasable secured to the arm or leg by at least one hook and loop type fastener.

9. An apparatus according to claim 3, wherein said hand or foot treatment chamber is a bottle-shaped chamber having a larger lower open end and a smaller threaded upper end.

10. An apparatus according to claim 3, wherein said air treatment device includes a bottle-shaped chamber having an upper threaded end and a lower open end, said air treatment chamber containing said fan, air dryer and air heater.

11. An apparatus according to claim 10, wherein said fan being an electric powered fan disposed within said air treatment chamber, said air dryer being at least one heating coil disposed adjacent said fan, and said air dryer being a layer of air drying composition disposed within said chamber.

12. An apparatus according to claim 11, wherein said air treatment chamber is supported on a base stand.

13. An apparatus according to claim 11, wherein said air treatment chamber includes a one-way valve.

14. An apparatus according to claim 3, wherein said air treatment chamber includes a one-way valve.

* * * * *